United States Patent [19]

Moore

[11] Patent Number: 5,328,844
[45] Date of Patent: Jul. 12, 1994

[54] CULTURE MEDIA FOR MAMMALIAN CELLS

[75] Inventor: George E. Moore, Conifer, Colo.

[73] Assignee: University of Colorado Foundation, Inc., Boulder, Colo.

[21] Appl. No.: 902,804

[22] Filed: Jun. 24, 1992

Related U.S. Application Data

[63] Continuation of Ser. No. 521,083, May 9, 1990, abandoned.

[51] Int. Cl.$^5$ .................. C12N 1/00; C12N 5/00; C12N 5/06
[52] U.S. Cl. .................. 435/240.31; 435/240.1; 435/240.2; 435/240.21; 435/240.23; 435/240.3; 435/244; 424/531; 514/2; 514/21
[58] Field of Search .......... 435/240.3, 240.31, 244, 435/240.1, 240.2, 240.3, 240.3, 240.21, 240.23; 424/531; 514/2, 21

[56] References Cited

PUBLICATIONS

Ohmori, J. Immunological Methods 112 (1988) 227–233.
Barnes, Cell 22 (1980) 649–655.
Mizrahi, Appl. Microbiol. 19:906–910.
Sigma, Cell Culture Reagents 1993 Catalogue Price List (published 1992) Sigma Chemical Company, St. Louis, Mo.
Moore et al. (1967) J. Am. Med. Assoc. 199:519–524.
Beebe et al. (1987) Cancer Res. 47:2380–2384.
Moore and Woods (1977) Tissue Culture Assoc. Manual 3:503–509.
Simms et al. (1980) Cancer Res. 40:4356–4363.
Darbre et al. (1984) Cancer Res. 44:2790–2793.
Soyano et al. (1985) Immunol. Lett. 9:57–62.
Roth et al. (1988) In Vitro 24:696–698.
Brower et al. (1986) Cancer Res. 46:798–806.
Zhu et al. (1984) In Vitro 20:615–622.
Carney et al. (1981) Proc. Natl. Acad. Sci. USA 78:3185–3189.
Kagan et al. (1980) J. Immunol. Meth. 37:15–27.
Needleman et al. (1981) J. Immunol. Meth. 44:3–14.
Jadus et al. (1988) J. Immunol. Meth. 109:169–174.
Hwang et al. (1985) J. Receptor Res. 5:27–43.
Shaw et al. (1987) J. Virol. 61:4033–4037.
de Groot et al. (1983) Thrombosis Res. 31:623–634.
McEvoy et al. (1982) Endocrinology 111:1568–1575.
Gregerson et al. (1975) Immunology 29:237–246.
Kristensen et al. (1982) Scand. J. Immunol. 16:209–216.

*Primary Examiner*—Michael G. Wityshyn
*Assistant Examiner*—Jane Williams
*Attorney, Agent, or Firm*—Greenlee & Winner

[57] ABSTRACT

The present invention provides a culture medium designated COF 1769 useful for establishing, growing and maintaining mammalian cells in culture, in particular for the establishment and culture of human normal and malignant cells. Also provided by the invention is an improved method for obtaining growth of mammalian cells.

9 Claims, No Drawings

CULTURE MEDIA FOR MAMMALIAN CELLS

This application is a continuation of application Ser. No. 07/521,083, filed May 9, 1990 now abandoned.

FIELD OF THE INVENTION

The present invention relates to the field of tissue culture media useful for the in vitro growth of mammalian cells.

BACKGROUND OF THE INVENTION

The growth and maintenance of cells derived from animal and human tissues and the establishment of cell lines are important for many different purposes. For example, tissue culture is used extensively for the production of enzymes, cell products such as the lymphokines, plasminogen activator, antibodies etc., and for the general testing of drugs, carcinogenic and chemotherapeutic agents and the like, and in studies of infectious diseases, cancerous diseases, and inherited or acquired disorders. With the development of cell fusion and the preparation of monoclonal antibodies, a directed emphasis has been placed on in vitro growth of animal and human cell lines for the development of diagnostic tests. Cultured human cells themselves are being used for the therapy of cancer patients by various kinds of adoptive immunity.

It is well-known that specific cell lines can be grown in vitro in optimally formulated culture or nutrient media (Hanss et al. (1964) Exp. Cell Res. 34:243-256; Fahey et al. (1966) Science 152:1259-1261; and Ham and McKeehan (1979) Methods in Enzymol. 58:44-93). Some examples of culture media developed for special purposes are: RPMI 1640 medium for optimal growth of human B-lymphoid cells (Moore et al. (1967) J. Am. Med. Assoc. 199:519-524) and diverse kinds of malignant cells, Changs medium for optimal growth of amniotic fluid cells, medium 199 for optimal growth of mouse fibroblast cells, MEM medium, a "minimal" medium for optimal growth of attached mammalian cells, Leibovitz medium for optimal growth in absence of $CO_2$, F10 medium for optimal growth of liver cells, etc. Such media are distinguished from one another in that they contain critically different components in precise amounts. These components include amino acids, vitamins, inorganic salts, trace elements and other organic compounds which promote the maximum growth of the cultured cells. For most purposes media are supplemented with serum.

The growth of various mammalian cells in vitro has been achieved in several chemically defined media supplemented with various sera, preferably fetal calf or newborn calf serum and other incompletely defined growth factors. Unfortunately, the addition of serum, whose constituents may vary widely, introduces undefined biological components into the nutrient medium and, hence, contributes to the variability of biochemical and cellular events. Furthermore, serum is expensive and in some instances, has been shown to be inhibitory to the growth of certain cells and may result in critical immune reactions in patients if the cells are used for clinical purposes.

The possibility of growing certain types of cells in serum-free medium was undertaken by several laboratories, e.g., Sato (1975) in *Biochemical Actions of Hormones*, G. Litwack (ed.), Academic Press, New York, Vol. 3, pp. 391-396; Bottenstein et al. (1978) Methods in Enzymol. 58:94-108; Beebe et al. (1987) Cancer Res. 47:2380-2384; Cole et al. (1987) J. Immunol. Meth. 97:29-35; Ham et al. (August 1988) *In Vitro* 24:833-844). Replacement of serum with supplements of better defined composition was found to be not very successful for the growth of normal cells in conventional culture media, although in vitro growth of some kinds of malignant cells was supported under these conditions after a period of adaptation. Only relatively slow growth of a selected few kinds of cells was possible in the absence of supplemental proteins.

Gradually, the amount of undefined supplementation needed for good growth was reduced by a process of optimization in particular basal nutrient media for selected cell lines (Mizrahi et al. (1970) Appl. Microbiol. 19:906-10; Ham (1984) in Methods for Preparation of Media, Supplements and Substrata for Serum-Free Animal Cell Culture, Alan R. Liss, Inc., New York, pp. 3-21). Moore and Woods (1977) Tissue Culture Assoc. Manual 3:503-509 expressed the generally held tenet in the art that "Some media will be better for initiating cultures of fresh cells while others will be better suited for maintaining established cell lines. Media that provide vigorous cell reproduction may suppress cell differentiation." These authors, like others in the field believed that the elements of a successful culture medium for mammalian cells were determined by the kind of cells to be cultured, unknown nutritional supplements, osmolarity, buffers and pH levels, gaseous mixtures and other environmental aspects of the culture unit. Thus, emphasis was placed on development of optimized formulation of culture media for specific purposes and for selected cell lines as well as for the formulation of general purpose media.

In the 1960's the RPMI 1640 culture medium was formulated (Moore et al. (1967) supra). This medium is still the most widely used today for culturing human normal and neoplastic B-lymphoid cells, malignant human cells and many other kinds of mammalian cells. RPMI 1640 supplemented with 10 to 20% heat-inactivated fetal bovine serum (FBS) is proficient for initiating many types of cell cultures, and maintaining established cell lines when supplemented with 10 or 5% FBS. These media were shown to be unusually good for culturing fresh human lymphocytes and for supporting cell cultures derived from mice, rats and hamsters (Moore and Woods (1977) supra). Subsequently, several other media, e.g., GEM 1717, COF 1755, COF 1759, COF 1767, etc. were formulated by Applicant. Each of these media differs from RPMI 1640 with respect to composition, concentration of components and final ratios among individual components. A number of these media are sold commercially and are widely used for experimental and long-term tissue cultures (see catalogs from commercial vendors of scientific and biological products, e.g., Sigma Chemical Company, St. Louis, Mo.; Gibco, Grand Island, N.Y.; Irvine Scientific, Santa Ana, Calif.; J.R. Scientific, Woodland, Calif.; Hazeton Biologics, Lenexa, Kans.; etc.).

Simms et al. (1980) Cancer Res. 40: 4356-4363 studied the supplemental growth factor requirements for replication of human small cell carcinomas of the lung in serum-free RPMI 1640 medium, and developed a formula containing selenium, hydrocortisone, insulin, transferrin and 17β-estradiol (known as Hites). The Hites combination added to RPMI 1640 medium devoid of serum supplementation supported optimum replication of cultured lung carcinoma cells. The cells replicated with approximately the same doubling times as in RPMI 1640 medium supplemented with 10% fetal calf serum but they exhibited a lower cell population density and a longer lag phase in Hites-supplemented medium.

RPMI 1640 was also the basis for other formulae of media to be used without serum supplementation. Darbre et al. (1984) Cancer Res. 44:2790-2793 utilized serum-free RPMI 1640 medium supplemented with penicillin, streptomycin, HEPES buffer, insulin, hydrocortisone, transferrin, 3,3',5-triiodo-L-thyronine, epidermal growth factor (EGF), fibroblast growth factor (FGF) and fibronectin to grow human mammary cancer cells in monolayer and suspension culture to test and compare the effects of estradiol and tamoxifen. The growth rate of the mammary cancer cells in this serum-free medium was adequate but slower than in medium supplemented with serum.

A serum-free medium was developed by Ohmori (1988) J. Immunol. Methods 112:227-233, which supported primary antibody responses by cultured murine lymphocytes. The medium used was RPMI 1640 supplemented with β-cyclodextrin, insulin, transferrin, albumin, low density lipoprotein, putrescine and L-alanine as substitutes for fetal serum. This serum-free medium supported the antibody response to sheep erythrocytes, trinitrophenyl-Ficoll or trinitrophenyl-lipopolysaccharide as efficiently as 10% fetal calf serum containing medium.

O'Donnell-Tormey et al. (1987) J. Exp. Med. 165:500-514 studied the metabolism of pyruvate in normal and malignant mammalian cells grown and maintained in serum-free RPMI 1640 supplemented with nonessential amino acids, penicillin, streptomycin and additional glutamine. Their work suggested that pyruvate and related α-ketoacids protect mammalian cells in culture against peroxide-induced cytotoxicity.

In vitro lymphocyte proliferation, primarily of B-cells, was shown to be optimal when RPMI 1640 culture medium was supplemented with 5 to 20% serum. Soyano et al. (1985) Immunol. Lett. 9:57-62 were able to decrease the level of serum added to RPMI 1640 medium to as low as 1% and still obtain an adequate proliferation of human peripheral blood lymphocytes. They further found that in serum-free cultures, wherein RPMI 1640 is supplemented with additional glutamine, penicillin, streptomycin, sodium bicarbonate, transferrin and albumin, the proliferation rate of lymphocytes was approximately 80% of that obtained in the presence of 1% human serum. These authors further observed that albumin and transferrin acted synergistically on the mitogen stimulation of human mononuclear leukocytes.

SUMMARY OF THE INVENTION

The present invention provides novel nutrient media, herein designated COF 1769, COF 1769-BC, COF 1769-AG and COF 1769-E3 optimized for the growth of mammalian cells. The media of the present invention are based on the optimized formulation presented in Table 1. In comparison to other prior art media, these new media compositions permit simplification of aspects of formulation, provide better buffering, and include unique combinations of supplements which afford improved conditions for the selective establishment and maintenance of both normal and malignant mammalian cells.

TABLE 1

| | RPMI 1640*# mg/l | COF 1769** mg/l | COF 1769-BC mg/l | COF 1769-AG mg/l | COF 1769-E3 mg/l |
|---|---|---|---|---|---|
| COMPOSITION OF RPMI 1640 AND COF 1769 | | | | | |
| Amino Acids | | | | | |
| L-Alanylglutamine | — | — | — | 300 | — |
| L-Arginine | 200 | 200 | 200 | 200 | 600 |
| L-Asparagine.H$_2$O | 56.82 | 60 | 60 | 60 | 180 |
| L-Aspartic acid | 20 | 20 | 20 | 20 | 60 |
| L-Cystine, disodium salt | 59.16 | 60 | 60 | 60 | 180 |
| L-Glutamic acid | 20 | 100 | 100 | 100 | 300 |
| L-Glutamine | 300 | 650 | 650 | — | 900 |
| Glycine | 10 | 10 | 10 | 10 | 30 |
| L-Histidine | 15 | 15 | 15 | 15 | 45 |
| L-Hydroxyproline | 20 | 20 | 20 | 20 | 60 |
| L-Isoleucine | 50 | 50 | 50 | 50 | 150 |
| L-Leucine | 50 | 100 | 100 | 100 | 300 |
| L-Lysine HCl | 40 | 60 | 60 | 60 | 180 |
| L-Methionine | 15 | 15 | 15 | 15 | 45 |
| L-Phenylalanine | 15 | 15 | 15 | 15 | 45 |
| L-Proline | 20 | 20 | 20 | 20 | 60 |
| L-Serine | 30 | 30 | 30 | 30 | 90 |
| L-Taurine | — | 20 | 20 | 20 | 60 |
| L-Threonine | 20 | 20 | 20 | 20 | 60 |
| L-Tryptophan | 5 | 5 | 5 | 5 | 15 |
| L-Tyrosine, disodium salt | 24.84 | 10 | 10 | 10 | 30 |
| L-Valine | 20 | 40 | 40 | 40 | 120 |
| Vitamins | | | | | |
| p-Aminobenzoic acid | 1 | 1 | 1 | 1 | 2 |
| Biotin | 0.2 | 0.2 | 0.2 | 0.2 | 0.4 |
| D-Calcium Pantothenate | 0.25 | 0.25 | 0.25 | 0.25 | 0.50 |
| Choline Chloride | 3 | 3 | 3 | 3 | 6 |
| Folic Acid | 1 | 1 | 1 | 1 | 2 |
| i-Inositol | 35 | 50 | 50 | 50 | 100 |
| Nicotinamide | 1 | 1 | 1 | 1 | 2 |
| Pyridoxine HCl | 1 | 1 | 1 | 1 | 2 |
| Riboflavin | 0.2 | 0.2 | 0.2 | 0.2 | 0.4 |
| Thiamine HCl | 1 | 1 | 1· | 1 | 2 |
| Thiamine Pyrophosphate | — | 1 | 1 | 1 | 2 |
| Vitamin B$_{12}$ | 0.005 | 0.005 | 0.005 | 0.005 | 0.01 |
| Salts | | | | | |

TABLE 1-continued

| COMPOSITION OF RPMI 1640 AND COF 1769 | | | | | |
|---|---|---|---|---|---|
| | RPMI 1640*# mg/l | COF 1769** mg/l | COF 1769-BC mg/l | COF 1769-AG mg/l | COF 1769-E3 mg/l |
| Ca(NO$_3$)$_2$.4H$_2$O | 100 | 100 | 100 | 100 | 25 |
| FeSO$_4$ | — | 0.1 | 0.1 | 0.1 | 0.1 |
| KCl | 400 | 400 | 400 | 600 | 700 |
| MgSO$_4$ (anhydrous) | 48.84 | 50 | 50 | 50 | 50 |
| MgCl$_2$ | — | 25 | 25 | 25 | 25 |
| NaCl | 6000 | 6000 | 6000 | 7000 | 6000 |
| NaHCO$_3$ | 2000 | 2000 | 2000 | — | 2000 |
| Na$_2$HPO$_4$ (anhydrous) | 800.76 | 400 | 400 | 400 | 400 |
| NaH$_2$PO$_4$ | — | 500 | 500 | 500 | 500 |
| ZnCl$_2$ | — | 0.1 | 0.1 | 0.1 | 0.1 |
| Miscellaneous | | | | | |
| BES*** | — | — | — | 4000 | — |
| Glucose | 2000 | 2000 | 2000 | 2000 | 3000 |
| Glutathione, reduced | 1 | 1 | 1 | 1 | 1 |
| Phenol Red | 5 | 5 (a) | 5 | 5 | 5 |
| β-Cyclodextrin | — | — | 100 | 100 | — |
| EGF*** | — | 0.005 | 0.005 | 0.005 | 0.005 |
| Ethanolamine | — | 12 | 12 | 12 | 12 |
| HEPES*** | — | 4500 | 4500 | — | 4500 |
| Hydrocortisone | — | 5 | 5 | 5 | 5 |
| Hypoxanthine | — | 15 | 15 | 15 | 15 |
| Insulin (zinc free) | — | 5 | 5 | 5 | 10 |
| 2-Mercaptoethanol | — | — | — | — | 0.5 |
| Oxalacetic acid | — | 150 | 150 | 150 | 150 |
| PIPES*** | — | 2000 | 2000 | — | 2000 |
| Sodium acetate | — | 50 | 50 | 50 | 50 |
| Sodium selenite | — | 0.005 | 0.005 | 0.005 | 0.005 |
| Sodium Pyruvate | — | 150 | 150 | 150 | 150 |
| 3, 3', 5-triiodothyronine | — | 0.001 | 0.001 | 0.001 | 0.001 |
| Transferrin (iron-saturated) | — | 5 | 5 | — | — |

(a) Phenol red is a pH indicator used at non-toxic concentrations which are not critical to growth.
*The pH of the medium is adjusted to pH 7.2 with 10% aqueous sodium carbonate solution.
**The pH of the medium is adjusted to pH 7.0 with 7.5% aqueous sodium carbonate solution.
***BES is the abbreviation for N,N-bis[2-Hydroxyethyl]-2-aminoethanesulfonic acid
EGF is the abbreviation for epidermal growth factor.
HEPES is the abbreviation for N-[2-hydroxyethyl]piperazine-N'-[2-ethanesulfonic acid].
PIPES is the abbreviation for 1,4-piperazinediethanesulfonic acid.
Moore et al. (1967) Am. Med. Assoc. 199:519-524.

COF 1769-BC represents a culture medium that comprises essentially the composition of COF 1769 but also includes B-cyclodextrin. Both COF 1769 and COF 1769-BC, without further requirement for serum supplements, support higher cell growth of selected mammalian cells than is observed in other prior art nutrient media with some serum supplementation. COF 1769-BC which contains β-cyclodextrin supports further enhanced cell growth compared to COF 1769. COF 1769 and COF 1769-BC, with or without serum supplementation, are superior to other comparable nutrient media in their abilities to sustain the quality and quantity of cell growth in culture. Both are useful for the growth of normal cells and are especially useful for the growth of human tumor cells. The media of the present invention are particularly useful for the effective establishment and maintenance of malignant cell lines from carcinomas, sarcomas, leukemias, lymphomas and gliomas as well as cell lines from normal cells, such as fibroblasts, B-lymphocytes and mesothelial cells.

COF 1769-AG represents a culture medium that comprises glutamine in the form of the dipeptide, alanylglutamine. COF 1769-AG differs from the basic COF 1769 medium not only in comprising alanylglutamine instead of glutamine but also in comprising an elevated level of glutamic acid and in utilizing BES (N,N-bis[2-hydroxyethyl]-2-aminoethanesulfonic acid) instead of the PIPES (1,4-piperazinediethanesulfonic acid)/HEPES (N-[2-Hydroxyethyl]piperazine-N'-[2-ethanesulfonic acid]) and bicarbonate buffer systems. As a result, the COF 1769-AG medium is a more stable medium than the basic COF 1769 medium for special application, e.g., for use in long-term mammalian cell cultures, with respect to maintenance of pH, a more constant supply of glutamine, and a lessened need for a high CO$_2$ atmosphere.

COF 1769-E3 represents a culture medium that is essentially that of COF 1769 except that the concentration of amino acids is increased approximately three-fold and the concentration of vitamins is increased approximately two-fold. The COF 1769-E3 medium offers a nutritional advantage to fresh mammalian cells, in particular during initiation of a new cell culture. A faster growth rate is observed for mammalian cells cultured in a more intense medium such as COF 1769-E3 than in COF 1769, especially during the early phase of establishment of the cell culture.

The four COF 1769 media differ from prior art media for culturing mammalian cells in the kind, amount and ratios of amino acids, salts, vitamins and growth factors, a lower pH, and an ease of preparation. For example, to prepare the basic COF 1769 medium, sixteen components were added to the basal RPMI 1640 medium, namely, epidermal growth factor (EGF), ethanolamine, HEPES, hydrocortisone, hypoxanthine, insulin, oxalacetic acid, PIPES, sodium acetate, sodium selenite, sodium pyruvate, taurine, thiamine pyrophosphate, thyronine, iron-saturated transferrin and zinc chloride. In addition, the altered concentrations and ratios of five amino acids (glutamine, leucine, lysine, tyrosine and valine) inositol, phosphate ion and magnesium ion were optimized in the new formulation of the nutrient medium.

There are available at present several serum-free culture media that employ RPMI 1640 as a basal medium to which a supplement of growth factors is added. However, these known serum-free media do not support mammalian cell growth to a higher extent than do the COF 1769 media with or without supplementation of optimal levels of serum. Applicant's present invention is an improved formulation over his previous formulation, RPMI 1640 medium, in that the four COF 1769 media without serum supplementation will support higher growth of some mammalian cells than is observed in RPMI 1640 culture medium with serum supplementation.

This invention also provides media compositions based on COF 1769 to which substitutions, deletions and additions can be made to optimize cell growth for specific purposes. Table 2 lists specific substances which can be added to COF 1769, COF 1769-BC, COF 1769-AG or COF 1769-E3 to achieve a desired purpose, e.g., to establish a specific cell line, e.g., epithelial cell lines, or to attain dedifferentiation, differentiation and manifestation of a specific function, e.g., production of specific antigens and antibodies.

TABLE 2

A partial list of acceptable additions to COF 1769

| Compound | Concentration Range |
| --- | --- |
| Alanine | 20-100 mg/l |
| Albumin (bovine) | 0.5-5 mg/l |
| Calcium ion | 25-300 mg/l |
| Catalase | 20-75,000 units/l |
| Cholera toxin | 0.001-0.01 mg/l |
| FeSO$_4$.7H$_2$O | 0.1-1 mg/l |
| Inositol | 10-100 mg/l |
| Linoleic acid | 4-10 mg/l |
| Mannitol | 200-1,000 mg/l |
| 2-Mercaptoethanol | 0.4-0.8 mg/l |
| Methocel | 0.1-0.2% |
| Polyvinylpyrrolidone-360 | 10,000-50,000 mg/l |

TABLE 2-continued

| Tris buffer system | approximately 10 mM |
| --- | --- |

(1) Alanine--This amino acid may aid cell growth immediately after culture but is usually unnecessary later in cell growth as most cells synthesize it.
(2) Albumin (bovine)--This protein may be added to serum-free media at levels varying between 0.5-5.0 grams/l. Human albumin may be toxic to particular cells. Some preparations of bovine albumin may be toxic to particular cells and should be pretested.
(3) The level of calcium ion may be decreased or increased according to the goals of the investigator. In general increased levels of calcium ion support cell differentiation and lesser growth rates.
(4) Catalase--It is sometimes used to reduce oxygen toxicity. The activity level of different preparations of catalase is variable.
(5) Cholera toxin--This may stimulate epithelial cell growth; however, the quality of available product is variable and the dosage should be experimentally determined.
(6) FeSO$_4$.7H$_2$O--Iron is added only if iron-saturated transferrin is deleted from serum-free media. Caution must be exercised to avoid precipitation during preparation by maintaining low pH. High concentrations of iron are toxic to cells in culture. Other iron salts have been used by various investigators, e.g., 0.05-0.15 mg/l of ferric citrate (Kovar (1988) Hybridoma 7:3.
(7) Myo-inositol--The concentrations of inositol may vary greatly; it is a useful growth stimulant for some epithelial cells and is relatively nontoxic.
(8) Linoleic acid--This is a common supplement in many serum-free cell culture media. However, it is relatively insoluble and is toxic to many cells and, therefore, is not a standard ingredient of COF 1769.
(9) Mannitol--This sugar is used as an anti-toxant and for its osmolarity. In concentrations of 200-1000 mg/l, it has supported increased cell growth in serum-free COF 1769. It is not metabolized.
(10) 2-mercaptoethanol--This compound has supported cell growth, especially of hematopoietic cells. There is evidence that it may act as an antioxidant and may increase the metabolism of cystine, especially in rodent cells.
(11) Methocellulose--It is believed (Mizrahi et al. (1970) Appl. Microbiol. 19:906-910) that the main function of synthetic polymers is protection of the cell membranes and may be similar to the protective effect of the mucopolysaccharides, which mammalian cells produce in vitro, bind to the cell surface and use as a protective agent. Different synthetic polymers may be used, for example, methyl cellulose, sodium carboxymethylcellulose, hydroxyethyl starch, dextrans, polyvinylpyrrolidones, modified gelatin, etc. These are particularly desirable for suspension cultures.
(12) Polyvinylpyrrolidone--It has been suggested (Leibovitz (1986) Cancer Genet. Cytogenet. 19:11-19) that polyvinylpyrrolidone helps to retain the cell viability when cells are exposed to harsh treatment. Presumably, its role is similar to the large serum protein molecules that provide physical protection to cells.
(13) Trace metals such as $Cu^{++}$, $Cr^{+++}$, $Co^{++}$, $Mn^{++}$, may be added as supplements in long-term cultures (Bettger et al. (1981) Proc. Natl. Acad. Sci. 78:5588-5592), but caution must be exercised as they may complicate precipitation problems and are toxic in minute amounts. They are unnecessary for serum supplemented media.
(14) Tris [tris(hydroxymethyl)aminomethane] buffer system comprising the approximate ratio of Trisma HCl$^R$ (Sigma Co., St. Louis, MO) 6.9 grams and Trisma base$^R$ (Sigma Co., St. Louis, MO) 0.8 grams per liter with a pH of about 7.0.

Thus, the media of the present invention can be used either as general purpose media, or, by modifications of the formulations, as special purpose media.

In addition, this invention provides semi-defined, serum-supplemented media for the growth of diverse normal and neoplastic mammalian cells. Specialized mammalian cell growth in culture is greatly facilitated when any of the four COF 1769 media are supplemented with not greater than 20%, and preferably about 2.5% (v/v) or less fetal bovine serum. The addition of even minimal amounts of serum to these media renders them improved for specialized growth of mammalian cells, particularly for the growth of specific human tumor cells. Moreover, the addition of a selected supplement or supplements of Table 2 to any of the four COF 1769 media renders them especially useful for culturing epithelial cells without serum. Supplemented COF 1769, COF 1769-BC, COF 1769-AG or COF 1769-E3 can also be used with about 2.5% (v/v) or less fetal bovine serum.

DETAILED DESCRIPTION OF THE INVENTION

According to Moore et al. (1977) supra, the elements of a successful culture medium for mammalian cells are determined by the kind of cells to be cultured, the serum supplement and the environmental aspects of the culture unit. There may be dramatic differences in the success rate of establishing cell lines when different medium formulations are used to initiate particular tissue cells in culture. The need for optimal division of cells in a brief time period soon disciplines one to use a particular combination of medium, serum components and supplements. There is little question of the desirability of maintaining a relatively constant environment for cultured cells, but the media and techniques for doing so in the past were simplistic, unreliable and affected only a limited number of factors such as pH, glucose levels, gas mixtures, etc. No simple electrolyte buffer mixture is best for all cells, and the addition of metabolites (e.g., oxalacetic acid and pyruvate) has been helpful, but only as a supplement to the usual buffers. Still, it is the applicant's contention that all kinds of normal and cancerous human cells with a continuing capability of reproduction in vivo should be cultivatable and our inability to do so reflects the primitive state of the art today and underscores the need to develop novel media and conditions which will enable the growth of all reproducible cells in culture.

Although many superficial changes in composition can be made to nutrient media known in the art, the creation of a novel nutrient medium requires that desired improvements will be obtained as a result of the formulation of a new medium. Some of the major difficulties encountered in the formulation of new media lie in determining optimal ratios among the many components that are required for cellular growth, distinguishing components that are critical for growth from those that act synergistically, and searching for components that are as yet untried or which are required only in trace concentrations. In the instant invention, culture media are formulated and optimized for the establishment and maintenance of effective mammalian cell growth in culture for either general or specialized purposes.

RPMI 1640, a widely used culture medium is a general purpose medium for supporting growth of mammalian cells in tissue culture. Although RPMI 1640 supports reasonably good growth of cells in culture, especially hemotopoietic cells, the culture media described herein are superior for the establishment and continued growth of mammalian cells in vitro for example, epithelial mammalian cells. The novel COF 1769 medium comprises the components listed in Table 1. COF 1769-BC medium contains essentially the composition of COF 1769 but with the additional presence of $\beta$-cyclodextrin. COF 1769-AG differs from the basic COF 1769 medium in employing alanylglutamine instead of glutamine, in comprising an elevated level of glutamic acid and in utilizing BES instead of the PIPES/HEPES and bicarbonate buffer systems. COF 1769-E3 is essentially the COF 1769 medium except that the concentration of amino acids is increased approximately three-fold and the concentration of vitamins is increased approximately two-fold. All four COF 1769 media comprise significant modifications and supplements compared to RPMI 1640. All four COF 1769 media are easy to prepare, relatively inexpensive and convenient to use and are useful as general purpose media for a wide variety of cells having different physiologic and pathologic states.

All four COF 1769 media favor the growth of human and animal cells. Cells from human tissues were the preferred test cells in studies leading to this invention. Both malignant and nonmalignant mammalian cells can be established more frequently and more easily maintained in these media as compared to other media, e.g., RPMI 1640, and MEM media. Cell lines from carcinomas, sarcomas, leukemias, and lymphomas are examples of malignant cells that were preferentially established and maintained in the media of the present invention. Of the nonmalignant cells cultured, some of the preferred cells for in vitro growth were, for example, lymphocytes, fibroblasts and mesothelial cells, and to a lessor extent, epithelial cells of various kinds.

The basic COF 1769 medium was developed by adding serum-free supplements to the RPMI 1640 medium one at a time or as multiples, in critical proportions, and assaying them over a wide range of concentrations to determine the optimal amount of each substance necessary to support improved in vitro growth of mammalian cells. An amount of a compound effective for cell growth in culture is defined herein as the amount of the compound determined experimentally to be optimal for the establishment and maintenance of effective mammalian cell growth in culture for a desired purpose. For a given required component of the culture medium, there is, in general, a plateau region in the growth response curve, where the substance has ceased to be the rate limiting factor for cellular multiplication due to deficiency, and where its concentration has not yet reached a level that is rate-limiting for cellular multiplication because of inhibitory or interference or toxic effects. The concentration plateau can be broad or narrow depending on the component tested, with the concentration of certain components being more critical to growth than other components. One of the objectives of optimization is to adjust the levels of all components of the basic nutrient medium to concentrations that are near the midpoints of their plateaus and at levels which will not adversely affect the optimal effects of other ingredients or provoke their precipitation or deterioration. Essentially the same procedures were used to formulate the derivative media COF 1769-BC, COF 1769-AG and COF 1769-E3 from the basic COF 1769 medium for promoting cell growth in culture under special conditions or for special purposes.

It was well-known in the art that addition of serum to supplement a nutrient medium improved animal or human cell growth in culture, and media containing up to approximately 20% fetal serum levels have been used by most investigators [Ham (1963) supra; Hauschka (1974) supra and Moore et al. (1967) supra]. Consequently, there was an emphasis in the art placed at (1) identifying the components in the serum that were beneficial to cell growth, and (2) utilizing the acquired information to create a serum-free culture medium that was equipotent to a culture medium supplemented with serum. In the formulation of the COF 1769 media, a series of growth assays were routinely conducted to evaluate the culture medium with serum concentrations not greater than about 20%, and preferably below about 5% and, more preferably, without serum. The test cells were human normal and malignant cell lines. Prior to evaluating the competency of media formulations to support cell growth, the test cells were maintained in a medium to which no serum or a minimum amount of serum was added. Such precaution avoided the possibility that cells which had been cultured with a high protein supplement would have protein bound to their membranes and, therefore, would continue to have higher growth rates for the first few days after transfer into serum-free medium (Moore and Woods (1977) supra). The quality of growth obtained in serum-free or serum-supplemented medium was evaluated routinely in order to attain optimized growth for diverse cells grown for general or specific purposes. A person of ordinary skill in the art is readily able to determine whether the establishment and maintenance of a specific cell line requires serum supplementation and to what level of supplementation.

In one embodiment of the invention, the basic COF 1769 medium was tested for competency in supporting cell growth either without serum supplementation or when supplemented with fetal serum at a level of about 2.5% or lower. As documented in Table 3, the COF 1769 culture medium without serum supplementation was found to support higher mammalian cell growth of selected cells, i.e., melanoma cells, than was supported by some other types of culture media with serum supplementation. Although it is preferable to use COF 1769 supplemented with a minimal level of serum, i.e., with approximately 1.0 to 2.5% serum, it is more preferable to use COF 1769 without serum supplementation for many studies, e.g., for the establishment of new cell lines. Also, although it is preferable to use bovine serum and is more preferable to use fetal calf serum, other types of sera from different mammalian sources can also be used. The ability to completely define a chosen nutrient medium reflects the most preferred environment for selecting cell culture conditions. Whenever serum is not added to a defined medium, there is no introduction of foreign protein into the culture medium and, hence, the likelihood that possible side reactions and virus infections might occur (if the cells are used for in vivo therapy) is minimized. Also, it is much easier to isolate unique cell products such as peptides and antibodies from serum-free media. Moreover, the expense of maintaining cell cultures is decidedly lower, if serum supplementation is not required. Finally, the tedium of pretesting each variable batch of serum for growth support and freedom from toxicity can be avoided.

PIPES and about 2000–7000 mg/l HEPES buffers be added and it is most preferred that the transferrin molecules be saturated with iron before being added to the optimized nutrient medium, COF 1769.

When optimal concentrations of all sixteen additives were combined with the basic RPMI medium, it was found that cell growth was still not optimal, due to the need to correct the concentrations of five amino acids, inositol, phosphate ion and magnesium ion that were a part of the original RPMI 1640 basic nutrient medium. It was found that higher concentrations of L-glutamine (about 350–950 mg/l), L-leucine (about 75–150 mg/l), L-lysine (about 50–80 mg/l) and L-valine (about 30–60 mg/l) were beneficial and that it is preferable to decrease the concentration of L-tyrosine (to about 2.5–35.0 mg/l) relative to the concentration levels of these amino acids in the original medium RPMI 1640. (Glycyl-L-tyrosine may be used to substitute for tyrosine in order to avoid solubility problems.) In addition, it is preferable to increase the level of inositol to between about 50 and 100 mg/l, phosphate ions to between about 850 and 1000 mg/l and magnesium ion to between about 65 and 85 mg/l. Table 1 indicates the differences in concentrations in these amino acids between RPMI 1640 and the COF 1769 media. Thus, as formulated, the four COF 1769 media contain the experimentally determined optimal concentration of each component for optimized general cell growth. In COF 1769-AG it is preferred that the increase in glutamine concentration be provided by addition of the dipeptide, L-alanylglutamine, which is a more stable source of glutamine for in vitro cultures. In long term cultures, glutathione may be added separately or supplementally to ensure full activity.

In the optimization of COF 1769-BC, it is preferred that between about 100 and 250 mg/l (and more preferably about 100 mg/l) $\beta$-cyclodextrin be added to the

TABLE 3

Comparison of Cell Growth in Different Culture Media With and Without Serum Supplementation

| Fetal Bovine Serum | Culture Medium | | | | |
|---|---|---|---|---|---|
| | RPMI 1640 | COF 1769 | F-12 | MEM | DMEM |
| | --Cell No. After Five Days in Culture-- | | | | |
| 0% | 1.86 × 10⁴ | 1.21 × 10⁵ | 2.41 × 10⁴ | 3.44 × 10⁴ | 1.28 × 10⁴ |
| | (15%) | (100%) | (20%) | (28%) | (11%) |
| 2.5% | 9.63 × 10⁴ | 2.36 × 10⁵ | 2.29 × 10⁵ | 1.14 × 10⁵ | 1.06 × 10⁵ |
| | (41%) | (100%) | (97%) | (48%) | (45%) |

A melanoma cell line, COLO 679, was grown in five different culture media, RPMI 1640, COF 1769, F-12, MEM and DMEM without and with 2.5% fetal bovine serum supplementation. The cells were cultured at 37° C. in an atmosphere of 5% carbon dioxide for five days. The starting cell count was approximately 10,000 cells per well.
Numbers in parentheses represent the percent increase in growth rate, i.e., the increase in number of cells over the number of cells present at time = 0.

During optimization of COF 1769 for growth of mammalian cells, it became clearly evident that several additional nutrient components were required to augment nutrient medium RPMI 1640 in order to support significantly improved cell growth. It is preferred that about 0.001–0.025 mg/l epidermal growth factor (EGF), about 5–35 mg/l ethanolamine, about 0.2–10.0 mg/l hydrocortisone, about 10–25 mg/l hypoxanthine, about 0.1–10.0 mg/l insulin, about 100–200 mg/l oxalacetic acid, about 25–75 mg/l sodium acetate, about 0.001–0.010 mg/l sodium selenite, about 100–200 mg/l sodium pyruvate, about 10–50 mg/l taurine, about 0.5–1.5 mg/l thiamine pyrophosphate, about 0.001–0.06 mg/l 3,3',5-triiodothyronine, about 0.05–15 mg/l transferrin and about 0.01–0.2 mg/l zinc chloride be added to RPMI 1640. It is more preferred that in addition to the above fourteen additives, about 1000–3000 mg/l basic COF 1769. In the formulation and optimization of the COF 1769-AG medium for long-term culturing of mammalian cells, it is preferred that glutamine, which is a component of the basic COF 1769 medium, be replaced by the addition of between about 150 and 450 mg/l (and more preferably about 300 mg/l) of alanylglutamine, and that the level of glutamic acid be between about 50 and 400 mg/l (and more preferably about 100 mg/l), and that the buffer consist essentially of between about 3000 and 5000 mg/l (and more preferably about 4000 mg/l) BES.

In the formulation and optimization of the COF 1769-E3 for use in the establishment of mammalian cell cultures, it is preferred that the concentration of all amino acids listed in Table 1 for COF 1769 be increased between about 1.5- and 4.5-fold (preferably about 3-fold) and the concentration of all vitamins listed in Table 1 for COF 1769 be increased between about 1.5- and 3-fold (preferably about 2-fold).

The use of an auxiliary buffer system in COF 1769, COF 1769-BC, COF 1769-AG and COF 1769-E3 media in addition to the bicarbonate/$CO_2$ and phosphate buffer systems was precautionary in nature. An auxiliary or "back-up" buffer system, preferably one containing HEPES buffer and, more preferably, one containing a HEPES/PIPES combination, was used to keep the pH of the medium at approximately pH 7.0, for example, in those situations where a 7.5% $CO_2$ atmosphere cannot be ensured, as for instance, when cell culture vials are removed from a regulated $CO_2$ source for experimental purposes. The back-up buffer maintains an acceptable pH level when the bicarbonate/$CO_2$ buffer system becomes inoperative. Other buffer systems equivalent to HEPES or PIPES in buffering range or capacity are known in the art and can also be used to function as back-up buffers in COF 1769. For example, BES buffer is used almost exclusively in the COF 1769-AG medium which is formulated for long-term culturing where stability and constancy in pH must be maintained over a long period of time. Tris [tris(hydroxymethyl)aminomethane]buffer at concentrations not to exceed 10 mM can also be used for this purpose. In COF 1769, COF 1769-BC and COF 1769-E3, it is preferred that a HEPES/PIPES buffer combination of about 6500 mg/l be included (or otherwise be substituted with sodium chloride or sodium chloride and mannitol to maintain desired osmolarity). The alteration of osmolarity by the addition of less than 5% serum is negligible. A final osmolarity of between 270 and 310 is preferred. If HEPES/PIPES or other buffer is reduced or eliminated, the sodium chloride or mannitol content is adjusted to a level no greater than 1000 mg/l in order to maintain a desired osmolarity of approximately 300 mosmoles. Mannitol is preferred for adjusting the osmolarity to an acceptable range. Small adjustments may be done with salts. Also, if additional buffer is used, the amount of sodium chloride is reduced. An osmolarity between 270-310 is acceptable; osmolarities above 350 are inhibitory. Although higher than for most commercial media, a 7.5% $CO_2$-air mixture is recommended for the COF 1769 media; the standard level of 5% $CO_2$ is acceptable for noncritical cultures. The preferred range of pH values for the COF 1769 media is between 6.8 and 7.3, with pH 7.0 being most preferred. Higher pH levels may cause an abnormal rise in intracellular pH values, which normally are less than 7.0.

A beneficial effect on cell growth by the addition of iron to the culture medium, for example, in the form of iron-saturated transferrin, was clearly observed. When iron saturated transferrin is used, no additional iron salts should be included in the medium. Zinc chloride was added, whenever zinc-free insulin was used. The combination of utilization of zinc-free insulin and addition of zinc chloride salt is preferred to the addition of insulin-bound zinc as this leads to variability in the level of zinc in the medium. Zinc is required for some enzyme activation. Most probably, the requirement for addition of low concentrations of metal ions and probably other trace ions results because they are present in other medium components at "contaminant" levels.

Selenium added to the culture medium as sodium selenite has been shown (Ham and McKeehan (1978) In Vitro 14:11) to be necessary for optimal cell proliferation in some cell cultures. Selenium is a cofactor for glutathione peroxidase, an enzyme which protects cells from toxic accumulation of peroxides (Morris et al. (1984) Science 223:491). In COF 1769 medium the optimal sodium selenite concentration was found to be approximately 0.005 mg/l.

Thiamine pyrophosphate was included in the formulation of COF 1769 because some cells in culture are unable to complete the metabolism of thiamine. Thiamine pyrophosphate is added at a preferred concentration of about 1 mg/l.

$\beta$-cyclodextrin, when added to CF 1769 medium in the concentration range between 100 and 250 mg/l, was found to have a significant effect on the growth rate of cells. Medium COF 1769-AG can be used without $\beta$-cyclodextrin because of its cost; however, in the presence of $\beta$-cyclodextrin, superior cell growth rates were observed. $\beta$-cyclodextrin has been shown to form inclusion complexes with various hydrophobic compounds and a role for $\beta$-cyclodextrin was suggested (Ohmori (1988) J. Immunol. Meth. 112:227-233) as a serum substitute in nutrient medium. The optimal concentration of $\beta$-cyclodextrin in COF 1769 medium was found to be approximately 100 mg/l. In one embodiment of this invention, 100 mg/l $\beta$-cyclodextrin was included in COF 1769 and found to be a superior culture media for promoting a higher rate of cell growth than in media without $\beta$-cyclodextrin supplementation as shown in Table 4.

The growth response of mammalian cells to varying amounts of transferrin indicated that the optimal range of concentration of transferrin is between approximately 1 mg/l and 10 mg/l, and is preferably 5 mg/l. Moreover, the preferred form of transferrin is the iron-saturated transferrin which may be obtained from regular commercial sources. When iron-saturated transferrin is incorporated into the formula, the addition of $FeSO_4$ or ferric citrate is not necessary. It is believed (Rizzino et al. (1979) supra; Taetle et al. (1985) J. Clin. Invest. 75:1061-1067) that a major function of transferrin is to act as an iron transport protein. It has been shown that the iron-transferrin complex must bind to the cell in order to supply the cell with iron.

TABLE 4

Effect of $\beta$-Cyclodextrin on Cell Growth in Culture Using COF 1769 Medium Without Serum

| $\beta$-Cyclodextrin mg/l | Relative Concentration of Cells in Culture Days in Culture | | |
|---|---|---|---|
| | Day 5 | Day 12 | Day 19 |
| 0 | 100 | 100 | 100 |
| 100 | 128 | 167 | 172 |

Adenocarcinoma cells at an initial concentration of $0.4 \times 10^6$ cells/ml were grown in COF 1769 medium with and without $\beta$-cyclodextrin. The concentration of cells in medium without $\beta$-cyclodextrin after the specified time interval was normalized to 100%.

Insulin has been found to act as an important beneficial additive to nutrient media with and without serum supplementation. The complete role of insulin in defined media has still not been resolved. Although insulin appears to be required by many cell types, the concentrations of insulin that produce optimal response for cell growth are approximately two orders of magnitude higher than typical blood concentrations of insulin. [Welborn et al. (1966) Lancet 1:280-284; Rizzino et al. (1979) supra.] It has been suggested that relatively large amounts of insulin are required because (i) either insulin binds weakly to cell receptor sites (Van Wyk et al.

(1979) in *Endocrinology*, Vol. 3, L. F. DeGroot et al. (eds.), Grune and Stratton, New York, pp. 1767-1775; and Roth (1979) ibid, pp. 2037-2054), or (ii) insulin is broken down in the culture medium. Testing for optimal concentration of insulin required in COF 1769 medium indicated a range of insulin concentration between approximately 0.1 mg/l and approximately 10 mg/l and preferably a concentration of approximately 5.0 mg/l. Moreover, use of zinc-free insulin is preferred so that a known amount of zinc can be provided as $ZnCl_2$.

Recently, studies by Boyd et al. (1988, Cancer Res. 48:2469-2474) indicated a synergy between insulin and transferrin in promoting cell growth in vitro. A subpopulation of human colonic carcinoma, HCT116, adapted to serum-free conditions, was responsive to transferrin but not insulin. Although insulin alone was without effect on these cells, when added together with transferrin, it increased growth by 600%. It was suggested that the synergistic effect between these growth substances may be a consequence of receptor modulation.

Epidermal growth factor (EGF) has been shown (Carpenter (1980) *Birth Defects* 16:61-72) to produce a variety of biologic responses in various cells, most of which involve enhanced proliferation and/or differentiation, and in some cases EGF may cause the maturation of some cells. Optimal cell growth was attained with a range of EGF concentrations between approximately 0.001 mg/l and approximately 0.025 mg/l, with the preferred concentration for most cell lines being approximately 0.005 mg/l. Due to the costliness of EGF in today's market, the COF 1769 media were prepared and tested in the absence of EGF. Omission of EGF from COF 1769 under test conditions of this invention resulted in a small but significant reduction in the mammalian cell growth in culture in some cases, but showed no effect under other circumstances. Although it is preferred to include EGF as a component in the COF 1769 media, each of the four COF 1769 media can be prepared without EGF and used as effective culture medium to establish and maintain mammalian cell growth. As is known in the art, EGF can be added later as a supplemental component to growing cell cultures. Thus, EGF can be added to cultures growing in COF 1769 media prepared without EGF, if it is so desired, without undue experimentation and as is taught in the instant disclosure.

The instability of the amino acid glutamine has been reported by several investigators (Eagle (1959) Science 130:432-437; Tritsch and Moore (1962) Exp. Cell Res. 28:360-364; Godel et al. (1984) J. Chromatogr. 297:49-61). Glutamine oxidation may contribute from 30 to 100% of the energy requirement of cells (Godel et al. (1984) supra; Reitzer et al. (1979) J. Biol. Chem. 254:2669-2676). Additionally, glutamine is unstable not only in aqueous solution but more so at incubation temperatures, forming pyroglutamate and ammonia, both of which are toxic for mammalian cells (Roth et al. (1988) In Vitro 24:696-698). Glutamine is the only amino acid for cell culture which must be added to the culture medium immediately before use, and replaced in stored media, and thus is added at 3 to 10 times greater concentrations than any other amino acid.

Roth et al. (1988) supra studied the effect of two glutamine-containing dipeptides, alanylglutamine (ala-glu) and glycylglutamine (gly-gln) on the growth behavior of a hematopoietic cell line in culture. These authors found that both ala-gln and gly-gln were biologically equivalent to glutamine. They also reported that whereas heat-sterilization of media containing glutamine caused approximately 95% decomposition of glutamine, both dipeptides remained unaltered. In the present invention (COF 1769-AG) use of ala-gln offers an advantage over glutamine use (i) in that the dipeptide (in contrast to glutamine) is stable during autoclaving and storage, (ii) in that the dipeptide is comparable to glutamine in biological activity, and (iii) in that it provides alanine which is not included in the basal medium. It is understood that there are other known dipeptides and tripeptides, having functional equivalence to ala-glu, that can be used in the practice of this invention.

Of the various types of cells grown in culture, epithelial cells, in particular, have presented a challenge for the establishment of cell cultures. Although it was shown by Vesterinen et al. (1980) Cancer Res. 40:512-519; Stanley and Parkinson (1979) Int. J. Cancer 24:407-410; and Shingleton and Wilbanks (1970) Am. J. Obstet. Gynecol. 108:28-33 that human epithelial cells can be grown in monolayer culture, many of these methods resulted in mixed populations of cells, cultures with a limited ability to be passaged or required fibroblast feeder layers or "conditioned" media. Recently, the requirement for a fibroblast feeder layer was obviated [Wright and Nahabedian (1986) J. Cell. Physiol. 126:10-20] when extended culture of rat epithelial cells was achieved by utilizing collagen gels and a complex growth medium, namely, a mixture of RPMI 1640 and Ham's F12 supplemented with 7.5% porcine serum and epidermal growth factor, cholera toxin, transferrin, insulin and hydrocortisone.

As a result of many assays and studies of media formulae resulting in this invention, i.e., the COF 1769 media, the culture of specific malignant epithelial cells was improved in specific cases by the addition of one or more supplements to any of the COF 1769 media, especially when used with less than 2.5% serum or without serum supplementation. Additives which were found to be beneficial for the growth of specific cells are listed in Table 2. These supplemental growth stimulants were not included in the basic formula of COF 1769 for several reasons:

(i) under some circumstances, some of the supplements were found to be toxic;

(ii) inclusion of some supplements had adverse effects, e.g., precipitation, on preparation of the final medium or during storage;

(iii) several of the supplements complicated technical aspects of cell recovery, altered growth rates, altered cell maturation and decreased recovery of cell products; and (iv) some compounds had a highly variable biological effectiveness.

(v) some compounds affected or altered the differentiation of cultured cells.

Additional compounds which have been shown to have sporadic or specialized effectiveness upon cell growth in specific circumstances when added to a medium of the instant invention are the following: α-ketoglutarate (about 100-500 mg/l), sorbitol (about 3,500 mg/l), acorbic acid (about 10-100 mg/l), pluronic F-68 (about 20 mg/l), glucagon (about 500 mg/l), hydroxyethyl starch (about 5,000 mg/l), retinol acetate (about 0.15 mg/l), menadione ($Na_2SO_3$) (about 0.02 mg/l), putrescine. HCl (about 0.1 mg/l), calciferol (about 0.1 mg/l), ribose (about 0.5 mg/l), thymine (about 0.3 mg/l), uracil (about 0.3 mg/l), xanthine (about 0.3 mg/l), adenine sulfate (about 10 mg/l), cholesterol (about 0.2 mg/l), deoxyribose (about 0.5 mg/l), guanine. HCl (about 0.3 mg/l), DL-α-tocopherol phosphate ($Na_2$) (0.01–10 mg/l), lactoalbumine hydrolysate (about 2,000 mg/l), glycyl-L-tyrosine (20–50 mg/l), bombesin (0.002–0.02 mg/l) and trace elements such as $CuSO_4.5H_2O$ (about 2.0 μg/l), $CoCl_2.6H_2O$ (about 1.5 μg/l), $MnCl_2.4H_2O$ (about 0.1 μg/l), $NiCi_2.6H_2O$ (about 0.1 μg/l), Molybdic acid.$4H_2O$ (about 1.2 μg/l) and $SnCl_2$ (about 0.1 μg/l).

Thus, all of the COF 1769 media can be used advantageously as either a general purpose medium or a specific purpose medium. For example, a cell line may first be established and grown in COF 1769 as a general purpose medium simply to maintain the cell line for a desired duration of time. Then, whenever these cells are to be grown for a special purpose, aliquots of these cells are transferred into a COF 1769 medium to which appropriate additive(s) are added, making the medium a more specialized medium for the intended purpose, for example, gene expression, production of a specific cell product, immunologic function, etc. In this way, COF 1769 medium offers an advantage over other types of media in that it can be used as a general purpose as well as a specialized medium. This is also the case for COF 1769-BC, COF 1769-AG and COF 1769-E3.

It was possible to establish primary cultures directly in any of the COF 1769 media of this invention without the need for conditioning of the medium or collagen coating of the walls, which were important features of at least one of the procedures used previously (Blau and Webster (1981) Proc. Natl. Acad. Sci. 78:5623–5627). Cells from biopsies and blood samples initially placed in a COF 1769 medium grew more readily and more often became established as cell lines. When desired, these cell lines were stored, preferably in the presence of 10–12.5% dimethylsulfoxide, with or without serum, and slowly frozen, preferably in liquid nitrogen or the vapor phase.

Studies done in the COF 1769 media with both non-malignant and malignant cells were focused on improvement of growth as well as on expression of differentiated properties. For example, one of the concerns was that overgrowth of epithelial cells by fibroblasts must be avoided and this concern was found to be minimized by utilizing media such as COF 1769 with minimal supplementation of serum or without serum.

In these studies cell growth was characterized by measuring percent viability and population doubling rates. Human cell cultures maintained in COF 1769 were found to have high viability, preferably a level of 85% or greater, and low population doubling times of between 6 hrs and 200 hours, depending on the cell type, and a preferred doubling time of about 20 hrs during the rapid growth of the malignant and nonmalignant human cells in Vitro.

Differentiation of cells grown in vitro in COF 1769 media was characterized on the basis of specific functionalities. Depending on the tissue source, different and distinguishing assays were performed to authenticate whether specialized functions were being maintained in specifically differentiated cells, for example, chromosome number, analysis of cell products (e.g., melanin production in cultured melanocytes), the presence of enzyme activities and/or isozyme patterns, the production of specific antigens and/or receptor sites, cell staining with immunological probes and other selected assays for specific cell types. In addition, some cells were characterized further by time-lapse video photomicroscopy, tumor cell cytotoxicity and phagocytosis.

The media described herein as COF 1769, COF 1769-BC, COF 1769-AG and COF 1769-E3 provide advantages over existing serum-free and low-serum culture media for many mammalian cells. The availability of an optimized all-purpose nutrient medium which will support growth of both human and animal and both normal and malignant cells will promote comparative studies useful for defining natural rather than media-induced differences between cells. In addition, the availability of the COF 1769 media will expedite comparative studies on the progression of differentiation and dedifferentiation in different cell types and, always an important consideration, will reduce the expense of conducting these studies by minimizing the number of different media required to study a maximal number of cell types. Furthermore, the ability to establish different mammalian cell lines and also to maintain these cell lines in the same highly defined medium such as COF 1769 with minimal supplementation of protein and other undefined components will facilitate more uniformly based lines of research that cannot readily be pursued at present for several reasons: (i) highly specialized media are required for distinct cell types, (ii) large amounts of whole serum must be added to a given medium and consequently render that medium "semi-defined," and (iii) long periods of adaptation to growth in serum-free media may be required. With the present formulation of COF 1769, a broad variety of cell lines can now be established, maintained and studied using the same basic medium.

The invention of the present application finds immediate medical application in those situations where human cells must be established and maintained for comparative studies of whole cells in both normal and abnormal states, for example, for karyotyping and other genetic expression characteristics, production of cell components such as hormone receptors, the generation of unique genetic expressions such as protooncogenes and oncogenes, and for studies of phagocytosis and cytotoxicity. A further application of the present invention is to establish and maintain fetal cell lines for application in fetal cell transplantation technologies, for example, for implanting fetal pancreatic islet cells or other endocrine cells, e.g., progesterone-secreting cells, into adults to supply missing biochemicals. The availability of fetal cell lines is particularly advantageous because fetal cells are less immunogenic than adult cells and may be directed toward a specific function.

Another goal of the present invention is provision of cell culture conditions useful for "adoptive cell therapies." This new approach to therapeutics utilizes adoptive autochthonous cells maintained and manipulated with pharmaceuticals in vitro rather than utilizing traditional pharmaceutical in vivo therapies. In vitro manipulations can comprise many different situations, for example, situations in which a patient's own cells are multiplied, pharmaceutically-treated and directed to retain and amplify cell functions and cell products, or expressions of genetic alterations before being returned to the patient. Situations may also exist in which cells are genetically engineered, multiplied and hybridized or fused, and perhaps pharmaceutically treated before being given to a patient. It is believed that adoptive cell therapies would be useful for diseases such as cancer, genetic diseases, diabetes and endocrine disorders, hemophilia, burns and AIDS and other infectious diseases requiring enhanced body defenses. The underlying technology critical for living cell therapy is the successful in vitro growth of mammalian cells. The medium of the present invention is useful for cell growth required in such applications.

In particular, this invention is a significant advance in the culture of immune competent autochthonous β-lymphoid cells, including macrophages which may be used for therapy of the human donor-patents. These cells will provide specific and non-specific immuno-globulins and/or phagocytic and cytotoxic activities and/or lymphokines and other cell products. The future utilization of these cells for therapeutic effects depends largely on the successful and rapid growth of such cells in vitro, and with minimal or zero exposure to proteins foreign to the donor/recipient patient, and with preservation and even enhancement of the cell functions.

It will be apparent to those in the art that certain changes in the specific chemical components employed in the preparation of a growth medium can be tolerated without affecting the function or altering the effectiveness of the medium. Also, it will be appreciated that certain non-nutrient materials, e.g., antibiotics, can be added to a growth medium without affecting the basic functionality of the medium. It will also be understood that certain components of the nutrient medium or the serum-free supplements can be substituted by equivalent substances or by preparations from different sources or with minor deviations of purity without affecting the functionality of the medium. Any such substitutions and additions are contemplated to be encompassed herein. Also, it will be understood that the nutrient medium of the instant invention can be prepared in a number of different ways known to those of ordinary skill in the art. For example, it can be prepared as one or more concentrated stock mixtures or solutions and then combined and diluted out as desired. Further, it is contemplated that the nutrient medium can be subjected to different physical treatments, for example, autoclaving, filtration, lyophilization, etc., and may be used as such with complete equivalence. Since modification of the specific embodiments will be apparent to those of skill in the art, it is intended that this invention be limited only by the spirit and scope of the appended claims.

The following examples are included for illustrative purposes only and are not intended to limit the scope of the invention.

EXAMPLES

Example 1: Preparation of Culture Medium COF 1769

A. Preparation of Stock Solutions (1) Preparation of. Stock.. Solution of Amino Acids The following 20 amino acids (excluding L-glutamine, which is frozen separately) were concentrated 2000 times in 100 ml volumes. For each amino acid, the correct amounts of dry chemicals (listed below) were added slowly to less than 100 ml of distilled-deionized water. In most cases 1 N HCl was required to solubilize the amino acids. The 100× stock was then frozen (−20° C.) in aliquots for later use. Distilled deionized water prepared according to FDA directives was obtained from Baxter Health Care Corporation, McGraw Park, Ill.

Amino Acids—Arginine, Asparagine, Aspartic acid, Cystine, Glutamic acid, Glutamine, Glycine, Histidine, Hydroxyproline, Isoleucine, Leucine, Lysine HCl, Methionine, Phenylalanine, Proline, Serine, Taurine, Threonine, Tryptophan, Tyrosine, Valine.

(2) Preparation of stock solution of vitamins

The following 10 vitamins were concentrated 100 times in a stock solution. Each vitamin was slowly dissolved with constant mixing (20 min or until a clear solution was obtained) in distilled-deionized water. The ten vitamin solutions were pooled in the order given below to make a 100× vitamin stock solution and then stored at 4° C. for later use. Vitamin $B_{12}$ and thiamine pyrophosphate were added separately.

Vitamins—calcium pantothenate, Inositol, Nicotinamide, Para-aminobenzoic acid (PABA), Pyridoxine HCl, Thiamine HCl, Riboflavin, Biotin, Choline chloride and Folic acid.

(3) Preparation of L-Glutamine Stock Solution

L-Glutamine was prepared as a 100× stock solution and was used in a ratio of 10 ml of stock per 1 l of final medium or 100 ml of stock per 10 l of final medium. The dry L-glutamine was dissolved slowly with constant stirring in 1.6 l of distilled-deionized water and filter sterilized. Because L-glutamine is heat labile, precaution was taken to immediately freeze solutions of the L-glutamine in 100 ml aliquots at −20° C.

(4) Addition of Vitamin $B_{12}$ and Thiamine Pyrophosphate

Commercially available sources of vitamin $B_{12}$ were employed.

Thiamine pyrophosphate was prepared as a stock solution concentrated 100-fold and stored at 4° C.. Calculated amounts of the stock solution were used as required.

(5) Preparation of Stock Solution of Salts

Each salt listed below was prepared as a 100× stock solution. The individual salt stock solutions were stored as noted below.

| Salt | Storage Temperature |
| --- | --- |
| Calcium nitrate.4 $H_2O$ | 4° C. |
| Ferrous sufate.7$H_2O$ | 4° C. |
| Potassium chloride | room temp. |
| Magnesium chloride (anhydrous) | 4° C. |
| Magnesium sulfate (anhydrous) | 4° C. |
| Sodium chloride | room temp. |
| Sodium dihydrogen phosphate (anhydrous) | room temp. |
| Disodium hydrogen phosphate (anhydrous) | room temp. |
| Sodium bicarbonate | 4° C. |
| Zinc chloride | room temp. |

(6) Preparation of Glucose Stock Solution

A 100× glucose stock was prepared and stored at 4° C. A calculated amount of stock was used to make a desired volume of final medium.

(7) Preparation of Indicator Stock Solution

Phenol red was prepared as a 100× stock solution, an aliquot of which was diluted appropriately before use.

(8) Preparation of Stock Solutions of Additional Components

Appropriate amounts of β-cyclodextrin, glutathione, ethanolamine, hydrocortisone, hypoxanthine, 2-mercaptoethanol, oxalacetic acid, sodium acetate, sodium pyruvate, taurine and zinc chloride were added from corresponding 100× stock solutions. Calculated amounts of sodium selenite, HEPES and PIPES were added from corresponding 100× stock solutions. Commercially prepared zinc-free insulin (Sigma Co., St.

Louis, Mo.) and transferrin in the iron-saturated form (Sigma Co., St. Louis, Mo.) were added to the medium preparation. Also, appropriate volumes of epidermal growth factor (EGF) and 3,3',5-triiodothyronine, obtained as sterile and cell culture tested commercial products, were added to the medium which was then adjusted to pH 7.0 and brought to final volume. The pH of added buffers such as HEPES, Tris, etc. are adjusted to pH 7.0 before adding appropriate aliquots to the media. An optimal osmolarity of approximately 300 mosmoles/l was attained by the addition of mannitol or adjustment in sodium chloride level. It was noted that in some assays more than 1000 mg per liter of mannitol is inhibitory to cell growth. Also, increasing osmolarity over 360 with sodium chloride was found to be inhibitory to cell growth. Inhibitory levels of mannitol and sodium chloride should be avoided. It should be noted that osmolarity adjustments are made after addition of buffer(s).

B. Preparation of Sterile Glassware and Hardware

The bottles in which the medium was distributed were cleaned by 10 rinses with tap water and six rinses with distilled-deionized water (obtained from Baxter Laboratories).

a. The bottles were dried by inversion in air or in a drying oven.

b. Each bottle was fitted with a small, thick strip of aluminum foil at the mouth and capped loosely before autoclaving. Distilled water to approximately 0.25-0.5% of the volume was added to ensure complete sterilization by autoclaving.

c. The bottles were placed in racks or baskets and the container was wrapped or labelled with autoclave paper or autoclave tape. The bottles were sterilized by autoclave (steam) for 30 min at 24 psi and 125° C. with a fast exhaust cycle. (The psi employed is increased at high altitude). Large bottles kept in an upright position are filled with a few ml of distilled water before autoclaving so as to ensure adequate sterilization of their interiors.

C. Preparation of Final Medium From Stock solutions

1. A vessel adequate to hold the desired volume of medium was thoroughly rinsed with distilled-deionized water and placed on a magnetic stirrer.

2. A stirring bar and the greater part of the calculated volume of distilled-deionized water was placed in the vessel.

3. Calculated amounts of the stock solutions were added with stirring in the following sequence: vitamins, amino acids, glutamine, $B_{12}$, thiamine pyrophosphate, glucose, salts indicator and all other supplements.

4. Most, but not all, of the water was added to the vessel and the medium was mixed slowly for a short time.

5. A suitable sample was removed for pH determination. To the sample was added gradually in 0.05 ml amounts either 1 N HCl or 1 N NaOH until pH 6.0 to 7.1, and preferably 7.0, was attained. The amount of HCl or NaOH needed to adjust the pH of the sample was used to calculate the amount needed to add to the total mixture. This calculated amount of HCl or NaOH and the remaining amount of water were added to the final volume and the solution mixed gently.

6. A sample of the final solution was then used for osmolarity measurements and adjustments, if necessary.

7. It is preferred that no antibiotics are added to the culture media and that rarely are antibiotics added directly to culture flasks. It is our experience that antibiotics rarely cure infected cultures and rarely prevent infections and, therefore, by omitting antibiotics, the dangers of transmitting occult infections of various organisms are minimized.

D. Filter Sterilizing The Medium

Several equally effective techniques of filtration and filling sterile bottles may be employed. All manipulations, for example, the dispensing of medium and the addition of serum supplement, were carried out in a sterile hood with a pre-checked air-flow filter.

Example 2: Establishment and Maintenance of Mammalian Cell Cultures

The COF 1769 culture media (or other commercial media used for comparison) without added serum or with varying levels of serum supplements were utilized for initiating mammalian cell cultures. All four COF 1769 media were unusually good for culturing fresh human lymphocytes, fibroblasts and mesothelial cells derived from ascites fluid, as well as cell cultures derived from mice and hamsters. Many human malignant cell lines—carcinomas, sarcomas, lymphomas—were also established and maintained. Furthermore, these media are useful for suspension cultures in containers ranging in volume from 5 ml to over 1000 l.

Clinical specimens were obtained from patients undergoing approved protocol staging (biopsies) or therapeutic procedures. Solid tumor specimens were mechanically disaggregated with fine scissors or scalpels. Additional cell separation was carried out with the aid of enzyme mixtures. Pleural or pericardial fluid was clarified with Ficoll-Hypaque density gradient centrifugation (Boyum (1968) Scand. J. Clin. Lab. Invest. (Suppl. 97) 21:77-109), or cells were collected by slow centrifugation. Some cultures were maintained with reduced oxygen. Tumor cell growth from clinical specimens was confirmed by determining morphology under phase contrast microscopy and by cytology.

The success rate for establishing cell lines from solid tumors of human origin was less than 5% as a whole, about 15% for malignant melanoma and 20% or more from effusions. In contrast to cells obtained from biopsy material, tumor cells that have established themselves in pleural or peritoneal effusions have membranes that can adapt to the immoderant changes associated with cell culture methodology and are more successfully cultured.

All cell growth experiments were done with cultures of mammalian cells prepared by serial subculturing of normal or abnormal cells desired in media with minimal or zero amounts of sera (Moore et al. (1967) supra). Primary cultures were grown until there were enough cells for characterization and freezing (about 20 population doublings), and then stored frozen, as described by Moore et al. (1967) supra. The normal human cells used preferentially for evaluating efficacy of different culture media were fibroblasts and $\beta$-lymphocytes. Some examples of malignant human cell lines used for assays of nutritional requirements are:

Colo 678—Colon carcinoma
Colo 684—Endometrial carcinoma
Colo 711—Malignant Melanoma (pigmented)
RPMI 7932—Malignant melanoma
Colo 679—Malignant Melanoma
Colo 677—Small cell lung cancer
Colo 320.DMF—Colon Cancer
Colo 680N—Esophagus squanous cancer RPMI 8226N—Myeloma
Colo 743—Mesothelioma
Colo 668N—Small cell lung cancer
Colo 737—Hodgkins Lymphoma
Colo 702—Lung cancer
Colo 704—Ovarian Cancer
Colo 710—Esophageal cancer
Colo 685—Adenocarcinoma
Colo 703—Ovarian cancer Ampules containing about one to two million frozen cells were thawed and distributed to 25 cm$^2$ flasks containing desired nutrient medium. The cultures were grown with medium changes as needed until they were semi-confluent, at which time individual flasks were used to prepare the inoculum for clonal growth experiments or subcultured and again grown to semi-confluency. Before the cellular inoculum was prepared, the test media were prepared and dispensed in commercially-obtained tissue culture petri dishes or multi-well plates. The dishes containing the media were then equilibrated in the cell culture incubator (37° C., 7.5% $CO_2$ in air, saturated humidity) for at least one hour.

To prepare the inoculum, the medium was removed from the culture flask and the cells were rinsed with 2.0 ml of 0.05% (w/v) trypsin plus 0.02% (w/v) EDTA in saline solution (pH 7.6) and then incubated in 2.0 ml of the same solution at room temperature until they were rounded up and beginning to release from the culture surface. The flask was then rapped sharply against the bench top to release the remaining cells and 2.0 ml of the medium into which they were to be inoculated was added. The suspension was centrifuged gently (1000×g for 3 min), the supernatant was discarded and the cells washed to remove excess enzyme solution. Some cell lines grow in suspension and therefore do not require enzyme treatment.

The cells were then resuspended in complete growth medium (or growth medium minus the component being tested). A sample was counted in a hemocytometer, and dilutions were made as needed to obtain the desired number of cells in a desired volume of inoculum. For many of the experiments described herein, growth-response experiments were done with 0.4×10$^6$ cells per ml.

Immediately after the inoculum was added, the dishes were swirled gently to ensure uniform distribution of the cells over the culture surface. The dishes were then incubated for up to 7 days without medium change. At the end of this period, the assay period can be lengthened by adding media. At various culture periods—3 days, 7 days, 14 days and even 21 days—the medium was discarded and the cells (0.5 ml) were added to 0.4 ml Trypan blue and 0.1 ml Versine for evaluation of growth.

Example 3: Cell Growth and Differentiation Assays

A. Attachment Factors

Precoating of tissue culture dishes with fetal bovine serum (FBS) was performed by adding 1 ml of culture medium with 10% (v/v) FBS to the dish, incubating the dish at 37° for 16 h, aspirating the serum-containing medium, and then washing twice with phosphate buffered saline (PBS). Precoating with fibronectin and collagen was accomplished by adding 1 ml of a solution of fibronectin (10 µg/ml) in culture medium to the dish for 16 h at 37° aspirating, and then adding 0.5 ml of Vitrogen and collagen (Flow Laboratories, McLean, Va.) diluted to a concentration of 100 µg/ml. The collagen containing solution was aspirated after further incubation for 24 h, and the dish was washed twice with PBS. Poly-D-lysine (type VII-B) and fetuin (type III) were obtained from Sigma Chemical Co., St. Louis, Mo. For most assays, precoating was not necessary.

B. Growth Factor Screening

For growth factor screening, cells in plateau phase growth in serum-supplemented medium were washed twice with PBS and then detached with a trypsin (1:250):EDTA solution in Hanks' balanced salt solution (GIBCO, Grand Island, N.Y.), which was then neutralized by addition of an equal volume of soybean trypsin inhibitor (0.5 mg/ml) Sigma) in PBS. Viable cell counts were determined by trypan blue exclusion in a hemocytometer. The viability of the cells as determined by trypan blue exclusion was routinely 85% or greater. Viable cells (5×10$^4$ cells) in 0.1 ml PBS were added to multiple well plates or tissue culture dishes with or without precoating and with an appropriate volume of the medium being tested. Cells were fed by replacing 50% of the spent medium every 4 days. After varying periods of days in the culture, the mean of triplicate counts of adherent cells for each treatment was determined by hemocytometer using light microscopy, and the cell density or ratio of cell number in medium plus the tested factor to the cell number in medium alone was determined.

C. Growth Studies

For growth curve and doubling time determinations, cells in log phase growth in various media were detached, seeded, and fed as above. Each point of a growth curve represents the mean of hemocytometer counts of the number of cells in three plates. Doubling times in log phase growth were then calculated. Cell lines maintained for long periods in serum-free medium were passaged with trypsin:EDTA solution neutralized with soybean trypsin inhibitor as described above (Moore et al. 1978). Other cell lines dissociated easily and did not require enzyme treatment.

Soft Agarose Cloning

For soft agarose cloning experiments, cells were harvested as described above, washed twice with PBS, and suspended in the test medium with 0.3% (v/v) agarose (SeaKem, Rockland, ME) at a concentration of 10$^4$ to 10$^5$ viable cells per ml. The mixture was then plated on each of three multi-well plates or culture dishes containing a base layer of the test medium with 0.5% (v/v) agarose that had hardened. Cells were incubated at 37° in a humidified atmosphere of 7.5% $CO_2$:92.5% air after initial inspection confirmed that a single cell suspension had been plated. Colonies of over 50 cells were counted at desired intervals after plating.

E. Morphology

Serial morphologic observations by phase optics were made of monolayer cultures grown on Leighton-tube coverslips as well as in special slide-culture flasks. Replicate coverslip preparations were stained with May-Grunwald-Giemsa, Papanicolaou, and Mucicarmine or other stains. Immune cytology preparations were for assays of hormone receptors and unique cell antigens, and cell products were prepared by cytospinning the cells onto glass slides.

Electron Microscopy

Specimens for scanning electron microscopy (SEM) were obtained by adding 2.5% glutaraldehyde in 0.1 M Nacacodylate buffer to the cultured cells, and the cells were rinsed 3 times with HEPES buffer. The cells were then postfixed with 1% $OsO_4$ in 0.1 M Na-cacodylate buffer, rinsed with the same buffer, dehydrated in increasing concentrations of ethanol, and dried. The specimens were then coated with a 200-A thick layer of gold and examined in a scanning electron microscope.

G. Cytogenic Analysis

Subcultures of the tumor cell line were harvested (2 to 6 months post-establishment) for chromosome preparations with standard cytogenetic procedures. Giemsa- and C-banding of the chromosomes were performed as previously described (Semple et al. (1978) Cancer Res. 38:1345–1355). Selected metaphase preparations were silver-stained for nucleolar organizer regions (NORs) according to the methods of Pathak and Hsu (1979) Chromosoma 70:195–203, and Bloom and Goodpasture (1976) Hum. Genet. 34:199–206. In addition, metaphase preparations were stained with Giemsa (pH 6.8) for elucidation of double minutes (DMs).

H. Assay for Psuedomosaicism

Trypsin-Giemsa banded metaphase chromosome preparations were analyzed microscopically. Pseudomosaicism was defined as a chromosomal abnormality that occurred in one (single cell abnormality) or more cells (multiple cell abnormality) in a primary culture [flask], but did not recur in either of two additional primary cultures [flasks] analyzed. Monosomic aneuploid cells other than 45,X were excluded from this analysis because such cells may be the result of disruption during processing or slide preparation. Cells with 45,X karyotypes were included as they may indicate mosaicism for Turner syndrome, and cannot be excluded as artifactual. The protocol which our laboratory follows as a minimum for distinguishing true mosaicism from pseudomosaicism (Hsu (1986) in *Genetic Disorders and the Fetus. Diagnosis, Prevention, and Treatment*, A. Milunsky (ed.) Plenum Press, New York, pp. 115–183) calls for establishing three or more culture vessels of amniotic fluid cells per specimen. Two of these vessels are routinely harvested and 10 cells are analyzed from each culture. If the abnormality involved a structural chromosome change in a single cell, then 10 additional cells are read from the flask without the abnormality making a total of 30. If a single cell is found with a numerical abnormality, a third flask is harvested and 20 cells are read from that flask and an additional 10 from each of the original two flasks, making a total of 60. If the same abnormality is detected in two different flasks the diagnosis of true mosaicism is made. If no other cells showing the same abnormality are seen, then the diagnosis of pseudomosaicism is made.

The attempt was made to score equal numbers of cells from cultures grown in the two media, but was found impractical because of growth variations. The data were evaluated statistically by a chi-square test in order to ascertain if differences in frequencies of pseudomosaicism could be the result of random variations.

I. DNA Synthesis

Aliquots of normal lymphocytes, cell lines, or leukemic blasts in 0.2 ml of complete or incomplete COF 1769 or RPMI 1640 media in the presence or absence of 10% FCS were added to 96-well microtiter plates (Costar, Cambridge, MA) at $2 \times 10^4$ cells/well. Normal lymphocytes were stimulated with 1 µg/well of phytohemagglutinin (PHA-P)(DIFCO Laboratories, Detroit, Mich.). Unstimulated lymphocytes served as controls. After 68-h incubations all cultures were pulsed 4 h with 1 µCi/well (specific activity, 20 Ci/nmol) of [methyl-$^3$H]thymidine (Amersham, Arlington Heights, Ill.). Cells were then harvested on glass filters (Microbiological Associates, Washington, D.C.) using a Mash II cell harvester (Microbiological Associates, Washington, D.C.) and washed with an excess of distilled water. Filters were transferred to scintillation vials containing 0.1 ml/vial of tissue solubilizer (Nuclear Chicago, Chicago, Ill.). After 1 h incubation at 37° C., 5 ml/vial of a toluene-based scintillation fluid were added, further incubated overnight in the dark, and counted in LS-150 liquid scintillation counter (Beckman Instruments, Inc., Irvine, Calif.) with counting efficiency of 45% (SE, 1%).

J. Biochemical Markers

Commercial kits were used to determine total creatine kinase activity (Sigma) and total protein (Biorad, Richmond, CA), and creatine kinase specific activity was calculated from the two values. In addition, creatine kinase isozyme distributions of selected cell lysates were examined with a commercial kit (Tital Gel-PC CPK-isozyme kit, Helena Laboratories, Beaumont, Tex.) to verify the relationship between increased specific activity and the presence of MB and MM isozymes.

A carcinoembryonic antigen (CEA) test kit (Roche Diagnostics, Nutley, N.J., U.S.) was used to assay the efficacy of different culture media in supporting cell growth in the presence and absence of serum supplements.

The production of both α-fetoprotein and the β-subunit of human chorionic gonadotropin (HCG) was measured in spent media from cultures and control medium by Consolidated Biomedical Laboratories (Wichita, Kans., U.S.).

To test for steroid hormone production, the tumor cell line was grown to near confluency (10 viable cells/4-oz culture flask). The culture medium was replaced for a 7-day period with 10 ml of culture medium with or without serum stripped of endogenous steroids by a 30-min incubation at 45° C. with a dextran-coated charcoal pellet (0.25% activated charcoal and 0.0025% dextran in 0.01 M Tris-HCl, pH 8.0 at 4° C. 1 ml/ml FBS). Culture medium with 5% hormone-stripped FBS was used as negative control.

Estrogen production was quantified with an Estrogen ($^3$H) ($E_1/E_2$) Radioimmunoassay Reagent Pak (New England Nuclear, Boston Mass.) progesterone and cortisol production were quantitated with a Progesterone ($^3$H) Radioimmunoassay Pak (New England Nuclear) and Cortisol ($^3$H) Radioimmunoassay Reagent Pak (New England Nuclear).

Adrenocorticotropic hormone (ACTH) assays were performed on 3-day-old spent RPMI medium 1640 with 10% FBS from actively growing cultures and on fresh complete medium without exposure to cultured cells. The ACTH was assayed by the method of Eipper and Mains (1975) Biochemistry 14:3836–3844.

Steroid hormone receptor proteins were measured as previously described (Woods et al. (1979) Methods Enzymol. 19:38–39; Stedman et al. (1979) Arch. Surg. 115:244–248). Specific receptor proteins for estrogen, progesterone, androgen and glucocorticoids werequantified using $^3$H-ligands of 17-β-estradiol, promegestone (R5020), 5-α-dihydrotestosterone, and dexamethasone, respectively.

Allelic isozyme (allozyme) phenotype of the cultured tumor cells was determined by the methods of Harris and Hopkinson (1976) *Handbook of enzyme electrophoresis in human genetics,* North-Holland Publishing Co., New York. The allozymes selected for phenotypic "fingerprinting" were glucose-6-phosphate dehydrogenase (G6PD), first and third locus of phosphoglucomutase (PGM$_{13}$), esterase D (ESD), "mitochondrial" glutamate-oxaloacetate transaminase (GOT$_m$), "red cell" acid phosphatase (ACP), and adenosine deaminase. Tumor cells were harvested by centrifuging, washed with phosphate-buffered saline and lysed with an equal volume of distilled water, then the cell-free supernatant was assayed directly.

The cultured tumor cells were tested for production of protease enzymes. Tissue culture medium was removed from two 75-cm$^2$ flasks of confluent cultured tumor cells and washed three times with phosphate-buffered saline. The washed cells were incubated in culture medium without serum for 20 h. The supernatant was concentrated five-fold with an Amicon concentrator using a membrane with a molecular exclusion limit of 10,000 daltons. Aliquots of the concentrated medium were assayed for trypsin (Erlanger et al. (1961) Arch. Biochem. Biophys. 95:271–278), elastase (Saklatvala (1977) J. Clin. Invest. 59:794–801), and chymotrypsin (Walsh and Wilcox (1970) Methods Enzymol. 19:38–39) using purified elastase, chymotrypsin and tosylphenyl chloromethyl ketone treated trypsin (Worthington Biochemicals, Freehold, N.J.) as protease standards. The synthetic substrates for these assays were α-benzoyl-DL-arginine-p-nitroanalide (Aldrich Chemical Co., Milwaukee, Wis.), α-benzoyl-tyrosine ethyl ester (Schwarz, Mann, Orangeburg, N.Y.) and succinyl-L-alanyl-L-alanine-p-nitroanalide (Bachem Fine Chemicals, Inc., Torrance, Calif.). Unincubated serum-free medium was used as a blank. Since some fetal bovine serum adheres to the cells and is recovered in the serum-free medium, 1% fetal bovine serum in serum-free medium was used as an additional blank. Malignant cells produce increased amounts of plasminogen activator (Lang et al. (1975) J. Nat. Cancer Inst. 54:173–179) which may result in increased plasmin in culture medium. Because plasmin hydrolyzes both arginine and lysine esters, the synthetic substrate used to measure tryptic activity could be hydrolyzed by plasmin. Therefore, the trypsin assay was made 0.1 M with epsilon-amino caproic acid (Sigma Chemical Co., St. Louis, Mo.), a specific inhibitor of plasmin (Robbins and Summaria (1976) Methods Enzymol. 45:257–286; Iwamoto et al. (1968) J. Biochem. (Tokyo) 64:759–767) to demonstrate that the hydrolysis was not due to plasmin activity.

K. Mycoplasma Tests

Tests for mycoplasma were made from smears of cultured cells stained with Hoecst 33258 fluorescent DNA stain according to the method of Chen (1975) Tissue Cult. Manual 1:229–232. Fluorescent observations were made using a Zeiss Photomicroscope III equipped with epi-illumination.

I claim:
1. A culture medium for establishing, growing and maintaining mammalian cells consisting essentially of the composition of the composition COF 1769 as defined in Table 1.
2. The medium according to claim 1 which further includes serum at a level not greater than about 2.5%.
3. The medium according to claim 1 which further includes serum at a level greater than 2.5% but not greater than about 20%.
4. A culture medium for establishing, growing and maintaining mammalian cells consisting essentially of the composition COF 1769 as defined in Table 1, but without epidermal growth factor (EGF).
5. The medium according to claim 4 which further includes serum at a level not greater than about 2.5%.
6. The medium according to claim 4 which further includes serum at a level greater than 2.5% but not greater than about 20%.
7. A culture medium for establishing, growing and maintaining mammalian cells consisting essentially of the composition COF 1769 as defined in Table 1 for the establishment, growth and maintenance of cells selected from the group consisting of human melanoma cells and human adenocarcinoma cells.
8. The medium of claim 7 for establishment, growth and maintenance of melanoma cells.
9. The medium of claim 7 for establishment, growth and maintenance of adenocarcinoma cells.

* * * * *

UNITED STATES PATENT AND TRADEMARK OFFICE
CERTIFICATE OF CORRECTION

PATENT NO. : 5,328,844
DATED : July 12, 1994
INVENTOR(S) : George E. Moore

It is certified that error appears in the above-indentified patent and that said Letters Patent is hereby corrected as shown below:

At column 14, line 12, please rewrite "CF" as --COF--. At column 16, line 62, please rewrite "500 mg/l" as --500 µg/l--. At column 17, line 7, please rewrite "NiCi$_2$" as --NiCl$_2$--. In claim 1, line 3, please delete the phrase "of the composition" positioned between "composition" and "COF".

Signed and Sealed this

Twenty-fourth Day of January, 1995

Attest:

BRUCE LEHMAN

Attesting Officer

Commissioner of Patents and Trademarks